(12) United States Patent
Coimbra

(10) Patent No.: US 11,058,623 B2
(45) Date of Patent: Jul. 13, 2021

(54) NON-THERAPEUTIC METHOD, USES OF A SUBSTANCE THAT STIMULATES OR GENERATES AN INCREASE IN VOLUME

(71) Applicant: Daniel Dal' Asta Coimbra, Rio de Janeiro (BR)

(72) Inventor: Daniel Dal' Asta Coimbra, Rio de Janeiro (BR)

(73) Assignee: Daniel Dal' Asta Coimbra, Rio de Janeiro (BR)

( * ) Notice: Subject to any disclaimer, the term of this patent is extended or adjusted under 35 U.S.C. 154(b) by 0 days.

(21) Appl. No.: 16/301,766

(22) PCT Filed: Dec. 1, 2017

(86) PCT No.: PCT/BR2017/050369
§ 371 (c)(1),
(2) Date: Nov. 15, 2018

(87) PCT Pub. No.: WO2018/098552
PCT Pub. Date: Jun. 7, 2018

(65) Prior Publication Data
US 2019/0175483 A1    Jun. 13, 2019

Related U.S. Application Data

(60) Provisional application No. 62/428,699, filed on Dec. 1, 2016.

(51) Int. Cl.
| | |
|---|---|
| *A61K 8/73* | (2006.01) |
| *A61K 31/155* | (2006.01) |
| *A61B 17/34* | (2006.01) |
| *A61K 31/167* | (2006.01) |
| *A61K 9/00* | (2006.01) |
| *A61Q 19/08* | (2006.01) |
| *A61B 17/00* | (2006.01) |

(52) U.S. Cl.
CPC .......... *A61K 8/735* (2013.01); *A61B 17/3421* (2013.01); *A61K 9/0019* (2013.01); *A61K 31/155* (2013.01); *A61K 31/167* (2013.01); *A61Q 19/08* (2013.01); *A61B 2017/00792* (2013.01); *A61K 2800/91* (2013.01)

(58) Field of Classification Search
CPC .... A61K 8/735; A61K 31/167; A61K 31/155; A61K 9/0019; A61K 2800/91; A61Q 19/08; A61B 17/3421
See application file for complete search history.

(56) References Cited

U.S. PATENT DOCUMENTS

| 8,252,348 B2 | 8/2012 | Buerger et al. |
| 2009/0155314 A1 | 6/2009 | Tezel et al. |
| 2012/0148649 A1 | 6/2012 | Giampapa |
| 2015/0182447 A1 | 7/2015 | Park |
| 2016/0038396 A1* | 2/2016 | Tezel ..................... A61K 47/42 424/94.67 |

FOREIGN PATENT DOCUMENTS

| EP | 2404642 | 1/2012 |
| EP | 2484387 A1 | 8/2012 |
| FR | 2948286 A1 | 1/2011 |

OTHER PUBLICATIONS

Paul Lorenc, Techniques for the optimization of facial and nonfacial volumization with injectable Poly-L-Lactic acid, Aesth plast surg (2012) 36: 1222-1229.*
Wilson et al, Current applications of facial volumization with fillers; Plastic and reconstructive surgery, vol. 137, No. 5, pp. 872e-889e, May 2016.*
Baker, A New and Better Face Lift Incision, Aesthetic Surgery Journal, pp. 428-430, (Year: 2000).*
Dr. DuPere, Use of cannula and dermal fillers is safe and less bruising, Cannula, Cannula, Cannula, Visageclinic.com. 1-3. (Year: 2014).*
International Search Report (English) and Written Opinion dated Feb. 15, 2018, from International Application No. PCT/BR2017/050369, 10 pages.
Belmontesi et al.; "Transdermal Injection of Restylane SubQ for Aesthetic Contouring of the Cheeks, Chin, and Mandible"; Aesthetic Surgery Journal—Jan./Feb. 2006, pp. S28-S34; 7 pages.
Wu et al.; "Novel Administration Technique or Large-Particle Stabilized Hyaluronic Acid-Based Gel of Nonanimal Origin in Facial Tissue Augmentation"; Aesthetic Plastic Surgery—Nov. 2009; dated Nov. 19, 2009; 9 pages.
European Search Report issued in Application No. EP 17875697.9; dated Jun. 15, 2020; 9 pages.

* cited by examiner

*Primary Examiner* — Mina Haghighatian
(74) *Attorney, Agent, or Firm* — Meunier Carlin & Curfman LLC

(57) ABSTRACT

The present invention aims to provide a non-surgical and non-therapeutic (cosmetic) method of dynamic three-dimensional facelift.

9 Claims, 1 Drawing Sheet

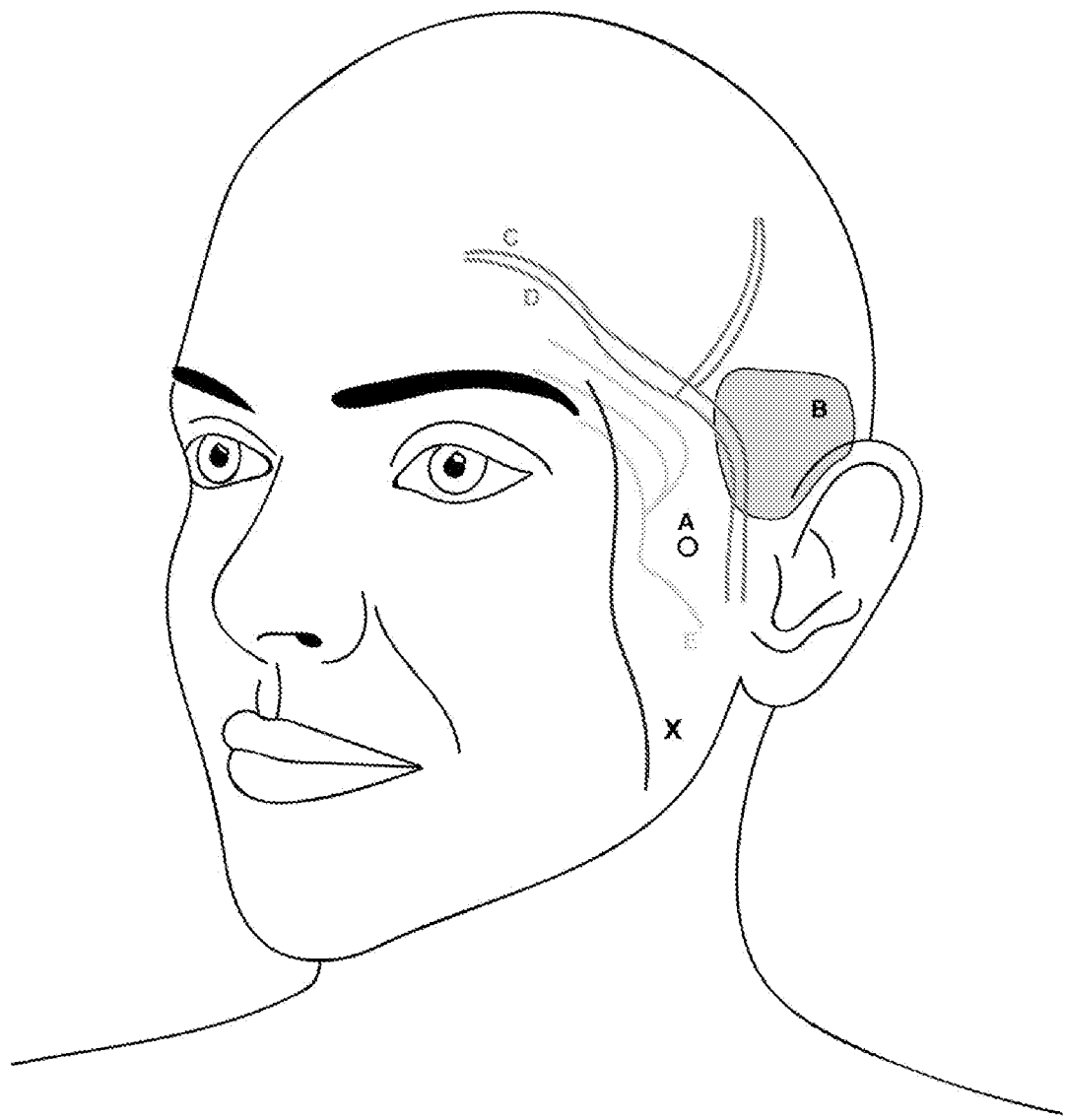

NON-THERAPEUTIC METHOD, USES OF A SUBSTANCE THAT STIMULATES OR GENERATES AN INCREASE IN VOLUME

FIELD OF THE INVENTION

The present invention relates to a non-therapeutic (cosmetic) method for performing a dynamic three-dimensional facelift through the application of substances that directly or indirectly stimulate or generate the increase of the volume in the supra-auricular region, in order to provide both static and dynamic rejuvenation of the entire face. More specifically, the non-therapeutic method of this invention utilizes substances which directly or indirectly stimulate or generate the increase of the volume in said region, such as hyaluronic acid, consisting of a polysaccharide, glycosaminoglycan composed of alternating and repeating units of D-glucuronic acid and N-acetyl-D-glucosamine, with hydrophilic properties, as well as other fillers or biostimulators such as calcium hydroxylapatite, acrylate polymer, silicone, fat and poly-l-lactic acid, among others.

BACKGROUND OF THE INVENTION

The surgical facelift (or Ritidoplasty) has always been considered one of the main treatments of facial flaccidity, promoting facial rejuvenation since its appearance in the early 20th century. In 1920, Bettman improved the technique by describing the pre-auricular and temporal access that determined a more discreet scar similar to those obtained today.

With the passage of time, the evolution of techniques has brought increasingly natural results, but combined with risks, definitive and not always satisfactory repercussions, the surgical approach is limited to treating the consequences of aging in the vast majority of cases.

In the last decades, due to the better understanding of the facial aging process, mainly related to the description of the fat compartments and their related alterations over the years, besides the measurement of bone remodeling that occurs in the face, together with the development of new filler substances for the volumetric restoration and muscular reeducation produced by the botulinum toxin, a new era has been established in the treatment of facial rejuvenation, in which non-surgical facelifts have gained prominence, with surprising and natural results.

The search for substances that directly or indirectly stimulate or generate the increase of volume, such as fillers which provide safe, durable, predictable and natural effects, has resulted in the discovery of hyaluronic acid (HA), which is a polysaccharide (glycosaminoglycan composed of alternating and repetitive units of D-glucuronic acid and N-acetyl-D-glucosamine) with hydrophilic properties, which causes an increase in the injected tissue. The initial filling effect is directly related to the volume of the injected filler. However, studies have shown that there is an indirect effect when injected into the dermis, due to the activation of fibroblasts. The need for a filler for deep face applications (fat and/or periosteum just compartments) has led to the development of volumetric restorative hyaluronic acids, which present a higher concentration of hyaluronic acid and crosslinking than HA fillers used in the dermis or subcutaneous superficial. This brought greater durability and viscosity to the gel, generating an increase in its lifting capacity against skin pressure. The duration of volumetric restoration HA fillers generally ranges from 12 to 24 months.

With this, the use of volumetric restoration fillers has established a new era in the treatment of facial rejuvenation. The evolution of the techniques and the use of new products enabled a three-dimensional approach of the face, which stopped to give importance to wrinkles and expression lines and opted for a global treatment of the contour by volume restoration.

Currently, in addition to the three-dimensional static improvement of the face, it has been outstanding in the facial rejuvenation treatments with fillers, maintenance or improvement of facial movement, where facial expressions are considered key pieces in the choice of application sites. In this way, it ceases to be a static application to be a dynamic three-dimensional application based on facial mime, where the filler can hinder muscle contraction by mechanical block or facilitate muscle movement by a deep support effect, reducing the force required for the muscle to perform its contraction.

The document WO2013/067293, for example, refers to a filler comprising hydrogel with a form that is suitable for injection into human tissue, and a method for improving the aesthetic quality of a human tissue, such method comprising injecting a hydrogel composition into a human soft tissue, the hydrogel composition comprising water and a cross-linked macromolecular matrix, such matrix including hyaluronic acid cross-linked to a collagen component. However, according to said document, the application suggested and described is limited to the malar region, which would not promote a filler action on the face as a whole, acting only in the region where it is applied.

The document "Volumizing effect of a new hyaluronic acid sub-dermal facial filler: a retrospective analysis based on 102 cases", Raspaldo, 2008, also addresses the volumetric restoration with hyaluronic acids. However, the application occurs in the malar region.

Therefore, although non-therapeutic methods with the use of substances that directly or indirectly stimulate or generate the increase of volume, such as fillers, are described in the State of Art, it is still important to develop a non-therapeutic method that actually achieves to promote the global rejuvenation of the face contour, with a three-dimensional approach of it through the use of substances that directly or indirectly stimulate or generate the increase of volume applied in the supra-auricular region that results, therefore, in the static and, mainly, dynamic rejuvenation of the whole face.

SUMMARY OF THE INVENTION

This invention aims to provide a non-surgical and non-therapeutic (cosmetic) method of dynamic three-dimensional facelift.

One embodiment of the present invention relates to the non-therapeutic method of dynamic facelift by the application of substances which directly or indirectly stimulate or generate the increase of volume in the supra-auricular region, preferably said substances may be selected from the group consisting of: hyaluronic acid, consisting of a polysaccharide, glycosaminoglycan composed of alternating and repeating units of D-glucuronic acid and N-acetyl-D-glucosamine, with hydrophilic properties, other fillers or biostimulators such as calcium hydroxyapatite, poly methyl acrylate, silicone, fat and poly-l-lactic acid, among others.

In a preferred embodiment, the increase of volume is performed with volumetric replacement of hyaluronic acid in the supra-auricular region.

A further embodiment of the present invention relates to the use of substances that directly or indirectly stimulate or generate the increased of volume in the supra-auricular region, preferably the volumetric replacement of hyaluronic acid, in non-therapeutic treatment to promote overall facial rejuvenation, both static and dynamic.

The features of the invention will be described in more details below.

BRIEF DESCRIPTION OF THE DRAWINGS

FIG. 1—application scheme in the face of volumetric replacement of hyaluronic acid according to a preferred embodiment of the method of the present invention.

DETAILED DESCRIPTION OF THE INVENTION

In this description, a non-therapeutic method of dynamic three-dimensional facelift for the promotion of overall rejuvenation is presented.

The term "bolus" is defined in this Application as the amount of substance which directly or indirectly stimulates or generates the increase of volume applied in order to rapidly increase its volume at the site of application.

The term "volumetric replacement of hyaluronic acid (HA)" refers to the crosslinked hyaluronic acid, which has a higher viscosity, with a great capacity for lifting and deep tissue support, and which leads to increased volume.

Surprisingly, the inventors of the present invention have identified that the application of substances which directly or indirectly stimulate or generate the increase of volume in the supra-auricular region of the face promotes a greater and increased facelift, notably the static and, mainly, the dynamic rejuvenation of the face as a whole, as well as the beneficial changes in the movement of the facial mime, which cannot be achieved as a result of the methods previously described in the State of Art.

The ear is disposed over the temporal bone. The temporal region is formed by the temporal bone and it articulates with the occipital, parietal, zygomatic, sphenoid and jaw bones.

The layers of tissue in the temporal region are the skin, subcutaneous fat, superficial temporal fascia (STF), deep temporal fascia (DTF) and temporal muscle. The STF represents the continuity of the superficial aponeurotic muscle system (SAMS) of the face and the aponeurotic glandular system of the scalp. This multilaminated facial layer (also called temporoparietal fascia) is loosely adherent to subcutaneous fat and is closely associated with the frontal branch of the facial nerve and the superficial temporal vessels. The loose areolar tissue, called the subaponeurotic tissue, separates the STF from the DTF and is the dissection tissue commonly used in the surgical approaches of the temporal region.

The DTF is a dense layer of connective tissue that covers the temporal muscle, and is adhered to the superior temporal line. A few centimeters above the zygomatic arch, the DTF is divided into a superficial layer and a deep layer. Between these two layers of the DTF is the superficial temporal fat deposit, which is irrigated by the middle temporal artery. Towards the deep layer of the DTF lies the deep temporal fat deposit, which represents the upper extension of the adipose mouthpiece assembly. This extension passes superiorly and deeply to the zygomatic arch to lie between the deep layer of the DTF and the temporal muscle.

When approaching this region with the use of substances that directly or indirectly stimulate or generate the increase of the volume, we must pay attention to two noble anatomical structures: the superficial temporal artery and the temporal branch of the facial nerve.

The superficial temporal artery is a terminal branch of the external carotid artery. Its origin lies inside the parotid gland, and rises to cross the zygomatic arch about 10 mm anterior to the tragus. The superficial temporal artery branches numerous terminals, including the facial transverse, the medium temporal, the parietal and the frontal branches.

The temporal branch of the facial nerve emerges from the superior margin of the parotid gland, 1.7 cm anterior to the tragus and crosses the zygomatic arch to supply the upper and anterior auricular muscles; the frontal belly of the occipitofrontalis; and, most importantly, the upper part of the orbicularis oculi. The temporal nerve, which runs near the deep face of the STF, is superficial when it crosses the zygomatic arch and is loosely adhered to the adjacent facial layers. The vulnerability of the temporal branch is at the level of the middle third of the zygomatic arch. Afterwards, they continue towards the front-temporal region, always next to the deep face of SAMS, until penetrating the frontal muscle in its deep face. Its lesion causes palpebral ptosis and permanent difficulty raising the eyebrow.

The application of the substance that directly or indirectly stimulates or generates the increases of volume can be done at any point in the face region, which goes from the angle of the mandible to the temple, passing through the pre-auricular region (Region X as shown in FIG. 1). The said application occurs between the skin and the bone of the face, more specifically in the subcutaneous region.

The application of substances that directly or indirectly stimulate or generate the increase of volume anywhere in the face region, which goes from the angle of the mandible to the temple through the pre-auricular region (Region X as shown in FIG. 1) may be carried out by means of a needle directly or, through the use of cannula, wherein said cannula can be 18G, 19G, 20G, 21G, 22G, 23G, 24G, 25G, 26G or 27G. Due to the important vascular-nervous structures present in the temporal region, it is recommended the use of cannula for the application of substances that directly or indirectly stimulate or generate the increase of volume at any point in the region of the face, which goes from the angle of the mandible to the temple, passing through the pre-auricular region (Region X as shown in FIG. 1). It is important, however, that when the cannula is used to be introduced into said region, which goes from the angle of the mandible to the temple, passing through the pre-auricular region (Region X as shown in FIG. 1), the same is directed to the supra-auricular region (Region B as shown in FIG. 1).

The choice of the entrance orifice located in the zygomatic bone obligatorily results in going with a cannula through a path perpendicular to the great vessels (temporal artery and vein), which would minimize the risk of intravascular injection.

The preferred choice for volumetric replacement of HA (juvederm Voluma®-Allergan Inc., USA), occurred because the area of application was an area with great osteo-articular movement, requiring a malleable product, but with a great lifting capacity and deep tissue support.

Through the palpation of a depressed area in the temporal region covered by the hair and the lifting effect caused by the digital traction of the skin from this area to the parietal region, it was verified that the patients could benefit from the volumetric replacement with HA at the site. Using the method described here, it was performed the use of the substance that directly or indirectly stimulates or generates the increase of volume at any point in the face region, which goes from the angle of the mandible to the temple, passing through the pre-auricular region (Region X as shown in FIG. 1), towards the region where the volume increase will occur, specifically the supra-auricular region (Region B as shown in FIG. 1), with an immediate lifting effect of the entire face, with a decrease in the ptosis of the malar and nasolabial fats on the nasogenian sulcus, increase in the skin tension in the lower eyelid due to lateral traction, elevation of the labial commissures, and improvement of the mandibular contour. In addition to these static effects, surprisingly, there were an increase in the eyebrow tail, and during the smile movement, a greater breadth of the mouth (greater exposure of the lateral teeth) and an increase in the ocular opening, due to the decrease in the need of use of the lift muscle of the superior lip, in addition to discrete reduction of the hypertrophic platysmal bundles, promoting a non-surgical Dynamic three-dimensional Lifting®.

According to FIG. 1, and as already mentioned above, the cannula path is perpendicular to the temporal artery (C) and to the temporal vein (D). The FIGURE also shows the temporal nerve (E), which is a branch of the facial nerve.

Thus, the method of the present invention comprises the following steps:
  a) asepsis of the whole face and temporal region covered by hair;
  b) application of an amount of substance that directly or indirectly stimulates or generates the increase of volume in the subcutaneous, on both sides of the face, directed to the supra-auricular region (Region B as shown in FIG. 1).

Preferably, the method of the present invention comprises the following steps:
  a) asepsis of the whole face and temporal region covered by hair;
  b) perforation for the entrance of a cannula into any point of the face region, which goes from the angle of the mandible to the temple, passing through the pre-auricular region (Region X as shown in FIG. 1), on both sides of the face;
  c) introduction of the cannula through the hole as described in step (b);
  d) sliding of the cannula through the subcutaneous region;
  e) application of an amount of substance that directly or indirectly stimulates or generates the increase of volume in the region where the volume increase will occur, wherein said amount ranges from about 0.2 to 2.0 ml in the subcutaneous region, on each side of the face.

Most preferably, the method of the present invention features the steps according to the order of (a) through (g) shown below:
  a) asepsis of the whole face and temporal region covered by hair;
  b) perforation for the entrance of a cannula into the angle of the mandible, on both sides of the face;
  c) introduction of the cannula through the hole as described in step (b);
  d) sliding of the cannula through the subcutaneous region until it reaches the supra-auricular region (Region B, as shown in FIG. 1);
  e) application of a bolus ranging from about 0.05 ml to 0.2 ml of substance that directly or indirectly stimulates or generates the increase of volume in the subcutaneous in the region where the volume increase will occur, on both sides of the face;
  f) performing a digital pressure on the said bolus so that the substance that directly or indirectly stimulates or generates the increase of volume to disperse;
  g) conclusion of the application of about 0.15 to 1.8 ml of the substance that directly or indirectly stimulates or generates the increase of volume on both sides of the face in order to reach a total volume ranging from about 0.2 to 2.0 ml, on both sides of the face, with forward and backward movements of the cannula in the whole supra-auricular area, the anterosuperior limit being the area of hair implantation and the inferior limit being the tragus of the ear.

In another preferred embodiment of the invention, the method of the present invention presents the steps according to the order of (a) through (g) shown below:
  a) asepsis of the whole face and temporal region covered by hair;
  b) perforation for the entrance of a cannula into the pre-auricular region, on both sides of the face;
  c) introduction of the cannula through the hole as described in step (b);
  d) sliding of the cannula through the subcutaneous region until it reaches the supra-auricular region (Region B, as shown in FIG. 1);
  e) application of a bolus ranging from about 0.05 ml to 0.2 ml of substance that directly or indirectly stimulates or generates the increase of volume in the subcutaneous, in the region where the increase of volume will occur, on both sides of the face;
  f) performing a digital pressure on the said bolus so that the substance that directly or indirectly stimulates or generates the increase of volume to disperse;
  g) conclusion of the application of about 0.15 to 1.8 ml of the substance that directly or indirectly stimulates or generates the increase of volume on both sides of the face in order to reach a total volume ranging from about 0.2 to 2.0 ml, on both sides of the face, with forward and backward movements of the cannula in the whole supra-auricular area, the anterosuperior limit being the area of hair implantation and the inferior limit being the tragus of the ear.

In a still another preferred embodiment of the invention, the method of the present invention features the steps according to the order of (a) through (g) below:
  a) asepsis of the whole face and temporal region covered by hair;
  b) perforation for the entrance of a cannula into the temple region, on both sides of the face;
  c) introduction of the cannula through the hole as described in step (b);
  d) sliding the cannula through the subcutaneous region until it reaches the supra-auricular region (Region B, as shown in FIG. 1);
  e) application of a bolus ranging from about 0.05 ml to 0.2 ml of substance that directly or indirectly stimulates or generates the increase of volume in the subcutaneous, in the region where the increase of volume will occur, on both sides of the face;
  f) performing a digital pressure on the said bolus so that the substance that directly or indirectly stimulates or generates the increase of volume to disperse;
  g) conclusion of the application of about 0.15 to 1.8 ml of the substance that directly or indirectly stimulates or generates the increase of volume, on both sides of the face, in order to reach a total volume ranging from about 0.2 to 2.0 ml, on both sides of the face, with forward and backward movements of the cannula in the whole supra-auricular area, the anterosuperior limit being the area of hair implantation and the inferior limit being the tragus of the ear.

In a still more preferred embodiment of the invention, the method of the present invention features the steps according to the order of (a) through (g) below:
a) asepsis of the whole face and temporal region covered by hair;
b) perforation for the entrance of a cannula into the region (A), on both sides of the face;
c) introduction of the cannula through the hole as described in step (b);
d) sliding the cannula through the subcutaneous region until it reaches the supra-auricular region (Region B, as shown in FIG. 1);
e) application of a bolus ranging from about 0.05 ml to 0.2 ml of substance that directly or indirectly stimulates or generates the increase of volume in the subcutaneous, in the region where the increase of volume will occur, on both sides of the face;
f) performing a digital pressure on the said bolus so that the substance that directly or indirectly stimulates or generates the increase of volume to disperse;
g) conclusion of the application of about 0.15 to 1.8 ml of the substance that directly or indirectly stimulates or generates the increase of volume, on both sides of the face, in order to reach a total volume ranging from about 0.2 to 2.0 ml, on both sides of the face, with forward and backward movements of the cannula in the whole supra-auricular area, the anterosuperior limit being the area of hair implantation and the inferior limit being the tragus of the ear.

In an even more preferred embodiment of the invention, the asepsis in step (a) is performed with a 2% alcoholic chlorhexidine solution or non-alcoholic chlorhexidine or 70% alcohol; the cannula to be used may be a 21G, 22G, 24G or 25G cannula; the amount of bolus volumetric replacement of hyaluronic acid ranges from about 0.1 to 0.4 ml, more preferably from about 0.1 to 0.2 ml, considering the application on both sides of the face; and the substance that directly or indirectly stimulates or generates the increase of volume (volumetric replacement) has an anesthetic in its formula which may be selected from the group consisting of xylidine derivatives, such as, for example, lidocaine. The step (g) comprises the application of the remainder of the substance which directly or indirectly stimulates or generates the increase of volume, in an amount ranging from about 0.5 ml to 3.6 ml, considering both sides of the face, with forward and backward movements that can be from the bottom to the top or from the top to the bottom (fan movements), said movements always being slow and with little force.

The product is deposited in greater quantity in the region closer to the ear, in a more depressed area easily demarcated by digital palpation. The total applied amount ranges from about 0.6 to 4.0 ml, and more preferably ranges from about 0.6 ml to 2.8 ml, considering the application on both sides of the face.

EXAMPLES

The following examples illustrate the preferred but not limiting embodiments of the present invention. It is not to be understood, however, that they limit the scope of protection of the invention, which is exclusively defined by the Claims accompanying this disclosure.

Example 1: Technique 1

With the patient lying down at 60 degrees, after asepsis with 2% alcoholic chlorhexidine solution in the entire face and temporal region covered by the hair, we performed a hole for the cannula entrance in the temporal region on zygomatic bone, more specifically orifice A (according to FIG. 1). A 24G or 25G cannula is introduced through the orifice A (according to FIG. 1) and slid through the subcutaneous region until it reaches the supra-auricular region (Region B, according to FIG. 1), where between 0.3 and 1.4 ml per side (totaling from 0.6 to 2.8 ml) of volumetric replacement of hyaluronic acid with lidocaine is injected in its subcutaneous formulation. The technique is used as a fan for the entire supra-auricular area, with slow and with little force forward and backward movements, the anterosuperior limit being the area of hair implantation and the tragus of the ear the inferior limit. The product is deposited in greater quantity in the region closer to the ear, in a more depressed area easily demarcated by digital palpation.

Example 2: Technique 2

With the patient lying down at 60 degrees, after asepsis with 2% alcoholic chlorhexidine solution in the entire face and temporal region covered by the hair, we performed a hole for the cannula entrance in the temporal region on zygomatic bone more specifically orifice A (according to FIG. 1). A 24G or 25G cannula is introduced through the orifice A (according to FIG. 1) and slid through the subcutaneous region until it reaches the supra-auricular region (Region B, according to FIG. 1), where a bolus of 0.1 to 0.2 ml of volumetric replacement of hyaluronic acid with lidocaine in its subcutaneous formulation is injected, considering the application on both sides of the face. Digital pressure is then performed on this bolus so that the dispersion of the product produces anesthetic effect in the region. The remainder of the volume replacement of hyaluronic acid with lidocaine in its formulation with fan technique is followed for the entire supra-auricular area, with slow and with little force forward and backward movements, the anterosuperior limit being the area of hair implantation and the tragus of the ear the inferior limit. The product is deposited in greater quantity in the region closer to the ear, in a more depressed area easily demarcated by digital palpation. The amount applied ranged from 0.3 to 1.4 ml per side (totaling from 0.6 to 2.8 ml).

Example 3: Results

A total of 165 patients were treated, being 152 women (92%) and 13 men (8%). The age ranged from 24 to 84 years and the average age was 50 years. Within these patients, 33 (20%) had already performed facelift plastic surgery (Table 1). On the other hand, a total of 57 patients (34.5%) sought care for the first time and 108 (65.5%) were returning patients.

The amount of product used in the supra-auricular region (Region B according to FIG. 1) ranged from 0.6 ml to 2.8 ml of total injected product, being 1.68 ml the total average, not existing any statistical correlation between the age and the amount of product applied.

After the application, it was observed a significant improvement of the entire facial contour related to the lifting effect produced by the product deposited in the treated region, as well as the improvement and smoothing of the facial expressions, generating a static and dynamic rejuvenation of the entire face.

Despite the non-use of any topical block or anesthetic, the reported pain was mild, being considered moderate in some patients who have had been subjected to a surgical facelift at the site. The edema in the region was reported as imperceptible and in some cases there was the presence of local bulging due to hematoma during the application, which were immediately controlled by digital compression and did not appear on the skin in the days following the procedure.

All patients presented improvement in the photographic evaluation performed immediately after the procedure, and were instructed to return to their normal activities shortly after the procedure. No paradoxical sinking of the temple was observed due to a possible excess of product in the supra-auricular region.

TABLE 1 profile of the patients treated with the substance that directly or indirectly stimulates or generates the increase of volume.

| Features | Up to 49 years old (n1 = 85) | 50 years old or more (n2 = 80) | Total (n1 + n2 = 165) |
|---|---|---|---|
| Number of men | 10 (11.8%) | 3 (3.8%) | 13 (7.9%) |
| Number of women | 75 (88.2%) | 77 (96.2%) | 152 (92.1%) |
| First time (=yes) | 30 (35.3%) | 27 (33.8%) | 57 (34.5%) |
| Returning patient (=yes) | 56 (65.9%) | 53 (66.3%) | 109 (65.5%) |
| Had supra-auricular treatment? (=yes) | 85 (100.0%) | 80 (100.0%) | 165 (100.0%) |
| Supra-auricular (d + e) (total amount in ml) | 144.00 | 133.00 | 277.00 |
| Supra-auricular (d + e) (average amount in ml) | 1.69 | 1.66 | 1.68 |
| Minimum amount (in ml) | 0.60 | 0.30 | — |
| Maximum amount (in ml) | 2.00 | 2.60 | — |
| Treated zygomatic in addition to supra-auricular? (=yes) | 60 (70.6%) | 47 (58.8%) | 107 (64.8%) |
| Zygomatic (d + e) (total amount in ml) | 35.10 | 34.00 | 69.10 |
| Zygomatic (d + e) (average ml amount) | 0.59 | 0.72 | 0.65 |
| Treated malar in addition to supra-auricular? (=yes) | 18 (21.2%) | 15 (18.8%) | 33 (20.0%) |
| Malar (d + e) (total amount in ml) | 15.10 | 14.60 | 29.70 |
| Malar (d + e) (average amount in ml) | 0.84 | 0.97 | 0.90 |
| Tratou malar, Zygomatic e supra-auricular? (=yes) | 14 (16.5%) | 15 (18.8%) | 29 (17.6%) |
| Malar, Zygomatic and Supra-auricular (d + e) (total amount in ml) | 42.00 | 49.70 | 91.70 |
| Malar, Zygomatic and Supra-auricular (d + e) (average amount in ml) | 3.00 | 3.31 | 3.16 |
| Surgical Lifting (=yes) | 2 (2.4%) | 31 (38.8%) | 33 (20.0%) |
| Supra-auricular (d + e) (average amount in ml) | 1.30 | 1.64 | 1.62 |
| Zygomatic (d + e) (average amount in ml) | 0.80 | 0.70 | 0.71 |
| Surgical Lifting (=no) | 83 (97.6%) | 49 (61.3%) | 132 (80.0%) |
| Supra-auricular (d + e) (average amount in ml) | 1.70 | 1.68 | 1.69 |
| Zygomatic (d + e) (average amount in ml) | 0.40 | 0.25 | 0.35 |

The search for naturalness in facial rejuvenation, combined with better understanding of the aging process and the discovery of new techniques and substances that directly or indirectly stimulate or originate the increase of volume, such as fillers of volume replacement of hyaluronic acid, has led to results increasingly surprising, often compared to those obtained only through surgical facelifts.

The three-dimensional approach of the face with the use of substances that directly or indirectly stimulate or generate the increase of volume in the region as described in the present Application is a safe method with natural and long lasting results when properly used. One should have a deep knowledge of the anatomy of each region and the changes related to the aging process of each area, so that the treatment is early directed to the causes, such as volume replacement in fat or juxta-osseous compartments, in order to avoid, attenuate or postpone the consequences presented on the surface, such as skin lines and folds.

From the method of the present invention, in addition to the three-dimensional static improvement of the face, it was obtained the maintenance or improvement of the facial movement, in which the facial expressions are considered key pieces when choosing the application sites.

The invention claimed is:

1. A method of performing a dynamic three-dimensional facelift, said method comprising the following steps:
    a) performing asepsis of the whole face and temporal region covered by hair;
    b) creating a hole for the entrance of a cannula into any point of the face region which goes from the angle of the mandible to the temple, on both sides of the face;
    c) introducing the cannula through the hole;
    d) sliding the cannula through a subcutaneous region until it reaches a supra-auricular region (B); and
    e) depositing an amount of a filler to the supra-auricular region (B), via the cannula, that directly or indirectly stimulates or generates an increase of volume in a subcutaneous region of the supra-auricular region (B).

2. The method of claim 1, wherein the increase of volume in the subcutaneous region ranges from about 0.2 to 2.0 ml on both sides of the face.

3. The method of claim 1,
    wherein the face region of step b) is a region (A)
    wherein the cannula is slid through the subcutaneous region until it reaches the supra-auricular region (B);

wherein a bolus ranging from about 0.05 ml to 0.2 ml of the filler is applied to the supra-auricular region (B); and wherein the method further comprises i) performing a digital pressure on the said bolus so that the filler directly or indirectly stimulates or generates the increase of volume to disperse;

ii) applying about 0.15 to 1.8 ml of the filler that directly or indirectly stimulates or generates the increase of volume in the holes on both sides of the face, in order to reach a total volume ranging from about 0.2 to 2.0 ml, on both sides of the face, with forward and backward movements of the cannula in the whole supra-auricular area, the anterosuperior limit being the area of hair implantation and the inferior limit being the tragus of the ear.

4. The method of claim 1, wherein the hole for the entrance of the cannula in the temple region is located above the zygomatic bone.

5. The method of claim 1, wherein the cannula is 18G, 19G, 20G, 21G, 22G, 23G, 24G, 25G, 26G or 27G in size.

6. The method of claim 1, wherein the filler further comprises an anesthetic, wherein the anesthetic is lidocaine.

7. The method of claim 1, wherein the filler that is applied with fan technique in the entire supra-auricular region.

8. The method of claim 1, wherein the filler is applied with forward and backward movements, wherein said movements can be from the bottom to the top or from the top to the bottom.

9. The method of claim 1, wherein the filler is a polysaccharide.

* * * * *